US008716668B2

(12) United States Patent
Crijns et al.

(10) Patent No.: US 8,716,668 B2
(45) Date of Patent: May 6, 2014

(54) RADIATION DETECTOR AND RADIOTHERAPY APPARATUS

(71) Applicant: Elekta AB (publ), Stockholm (SE)

(72) Inventors: Sjoerd Crijns, Utrecht (NL); Maria Giulia Thompson, Redhill (GB); John Allen, West Sussex (GB)

(73) Assignee: Elekta AB (publ), Stockholm (SE)

( * ) Notice: Subject to any disclaimer, the term of this patent is extended or adjusted under 35 U.S.C. 154(b) by 0 days.

(21) Appl. No.: 13/622,101

(22) Filed: Sep. 18, 2012

(65) Prior Publication Data

US 2014/0081068 A1 Mar. 20, 2014

(51) Int. Cl.
*G01T 1/20* (2006.01)

(52) U.S. Cl.
CPC ........................................ *G01T 1/20* (2013.01)
USPC ..................................................... 250/363.01

(58) Field of Classification Search
CPC ........................................................ G01T 1/20
USPC .......................... 250/363.01, 361 R, 227.24
See application file for complete search history.

(56) References Cited

U.S. PATENT DOCUMENTS 3,058,021 A * 10/1962 Dunn ............................ 313/527
5,553,616 A * 9/1996 Ham et al. ..................... 600/316
6,125,335 A 9/2000 Simon et al. ...................... 702/85
8,044,359 B2 10/2011 Simon ....................... 250/370.07
2006/0291767 A1 * 12/2006 Andrews et al. ................ 385/13
2012/0205530 A1 8/2012 Beaulieu et al. ............ 250/252.1

FOREIGN PATENT DOCUMENTS

WO    WO 2012/036570    3/2012    ................ G01T 1/10

OTHER PUBLICATIONS

Axelsson et al., *Cerenkov Emission Induced by External Beam Radiation Stimulates Molecular Fluorescence*, Med. Phys. 38(7), 4127-4132; Jun. 2011.
Glaser et al., *LINAC Dose Profiling Using Cherenkov Emission Imaging*, Medical Physics, vol. 39, issue 6, p. 3704; Jun. 2012.
Nelms et al., *VMAT QA: Measurement-Guided 4D Dose Reconstruction On A Patient*, Med Phys, Jun. 2012; 39(7):4228-38.
Goulet et al., *High Resolution 2D Dose Measurement Device Based on a Few Long Scintillating Fibers and Tomographic Reconstruction*, Medical Physics, vol. 39 Issue 8.

* cited by examiner

*Primary Examiner* — David Porta
*Assistant Examiner* — Faye Boosalis
(74) *Attorney, Agent, or Firm* — Sunstein Kann Murphy & Timbers LLP

(57) ABSTRACT

The present invention provides a radiation detector which comprises a tube and detector elements distributed over the tube. Such an arrangement can be used to provide information on a radiation beam prior to interaction with a patient and after interaction with the patient. The detector is particularly compact and therefore suited to use with apparatus where space is restricted. By a particular arrangement of detectors and optical fibers, the detector can provide data at all angles of rotation.

15 Claims, 5 Drawing Sheets

RADIATION DETECTOR AND RADIOTHERAPY APPARATUS

TECHNICAL FIELD

The present invention relates to a radiation detector, and to a radiotherapy apparatus employing a radiation detector.

BACKGROUND

Radiotherapy involves the application of ionizing radiation to a target within a patient (e.g. a tumour) so as to damage the unhealthy cells within the target, eventually causing cell death through one or multiple exposures. The radiation is harmful to both the unhealthy tissue within the target and the healthy tissue which surrounds it, and thus much research has been focussed on maximizing the radiation dose within the target while minimizing the dose outside the target. For example, the radiation may be collimated into a particular shape so as to conform to the shape of the target or to some other shape which is desirable for treatment. Various devices can be employed in such a collimation, but the most common is the multi-leaf collimator.

It has long been a goal for those working in the field of radiotherapy to combine simultaneous imaging and therapy of the patient. This is expected to lead to improved accuracy of treatment, in that the precise location of a target area can be more accurately determined at any particular time.

One system which has been proposed to achieve simultaneous imaging and treatment combines a radiotherapy system with a magnetic resonance imaging (MRI) system. An example of such a system is shown in WO 2005/081842. The magnetic coil of the MRI system is split into two coils separated by a gap, and the therapeutic radiation beam is delivered to the patient through the gap.

Another means of imaging a patient during therapy is through the use of portal imagers. A portal imager typically comprises a flat panel detector with an array of detecting elements. The detector is placed opposite the therapeutic radiation source and provides a transmission image of the radiation beam substantially along the beam axis (i.e. back towards the therapeutic radiation source). The imager thus provides an image of the radiation beam cross section. The portal imager can also provide imaging data of the patient's anatomical structure. Such data is inherently low contrast due to the high energy of the therapeutic radiation (therapeutic radiation typically has an energy in the MeV range, while radiation used for imaging purposes typically has an energy in the keV range), but is nonetheless useful. The conventional portal imager thus performs two functions, providing a check on the shape of the radiation beam (and thus the positions of the leaves of the multi-leaf collimator or other collimating device) as well as its placement relative to the patient.

The MRI function of the system in WO 2005/081842 achieves high-quality imaging of the patient undergoing therapy, but provides no feedback on the shape of the radiation beam. A portal imager would provide such feedback, but the integration of a conventional portal imager (i.e. a flat panel detector) within an MRI system would be challenging due to the space restrictions imposed by the narrow bore magnetic coils.

SUMMARY OF INVENTION

According to a first aspect of the present invention, there is provided a radiation detector for use in a system having a source of radiation, the source of radiation generating a beam of radiation along a beam axis for intersecting with a patient or part of a patient, the radiation detector comprising: a hollow tube in which the patient or the part of the patient can be positioned, the hollow cylinder having a primary axis which, in use, lies transverse to the beam axis; and a plurality of optical fibres distributed over the surface of the hollow tube for detecting the radiation beam.

The plurality of optical fibres may be distributed over the surface of the hollow tube for detecting the radiation beam prior to its impact with the patient, and for detecting the radiation beam after its impact with the patient. The plurality of optical fibres may therefore be distributed over the surface of the hollow tube at least in a first area, for detecting the radiation beam prior to its impact with the patient, and a second area diametrically opposite the first area, for detecting the radiation beam after its impact with the patient. In other embodiments, the plurality of optical fibres may be distributed over substantially the entire surface of the hollow tube.

The plurality of optical fibres may comprise a first subset of optical fibres running substantially parallel to each other, and a second subset of optical fibres running substantially parallel to each other and transverse to the first subset of optical fibres. In this way, the interaction of the radiation beam with at least one fibre from each subset allows the radiation beam to be located. The first subset of optical fibres may run substantially orthogonal to the second subset of optical fibres.

In an embodiment, at least one of the first and second subsets of optical fibres runs at an angle which is oblique to the primary axis of the tube, and in this way these optical fibres may run along a helical path (when the tube is cylindrical).

The radiation detector may further comprise a plurality of read-out devices coupled to the plurality of optical fibres. The plurality of read-out devices may comprise a first subset of read-out devices arranged towards a first end of the hollow tube, and a second subset of read-out devices arranged towards a second end of the hollow tube. Particularly when at least one of the first and second subsets of optical fibres runs at an oblique angle to the primary axis of the tube, this allows the radiation detector to function at all angles of rotation of the radiation beam.

In an embodiment, the plurality of optical fibres scintillate upon interaction with the radiation beam.

The plurality of optical fibres may be embedded within a wall of the hollow tube, or arranged on an internal or external surface.

The hollow tube may be manufactured from a substantially radiolucent material, such as epoxy, in order to minimize undesired interaction with the radiation beam.

In an embodiment, the tube is cylindrical (i.e. has a circular cross section). In other embodiments, the tube may have any cross-section shape.

In another aspect of the invention, there is provided an apparatus, comprising: a source of radiation, for generated a radiation beam along a beam axis; a patient support, for supporting a patient; and a radiation detector comprising: a hollow tube in which the patient support can be arranged, the hollow cylinder having a primary axis which, in use, lies transverse to the beam axis; and a plurality of detector elements distributed over the surface of the hollow tube for detecting the radiation beam.

For example, the apparatus may be a radiotherapy apparatus, in which case the radiation beam has an energy intended to have a therapeutic effect (generally in the MeV range), or an imaging apparatus, in which case the radiation beam has an energy suitable for imaging (generally in the keV range). The radiotherapy apparatus may be combined with an MRI system, in which case the tube of the radiation detector can be placed inside, outside, or within the magnetic coils of the MRI system.

The detector elements of the radiation detector may comprise optical fibres, but in other embodiments may comprise an array of charge-coupled devices (CCDs) arranged over the surface of the tube. Scintillator crystals may be arranged singly or in blocks over the surface of the tube, which scintillate upon interaction with the radiation beam. Alternatively amorphous silicon detectors may be arranged over the surface of the tube (a thin layer of detector material, distributed in pixels over the surface of the tube, and integrated with amplifying circuitry, i.e. thin film transistors).

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
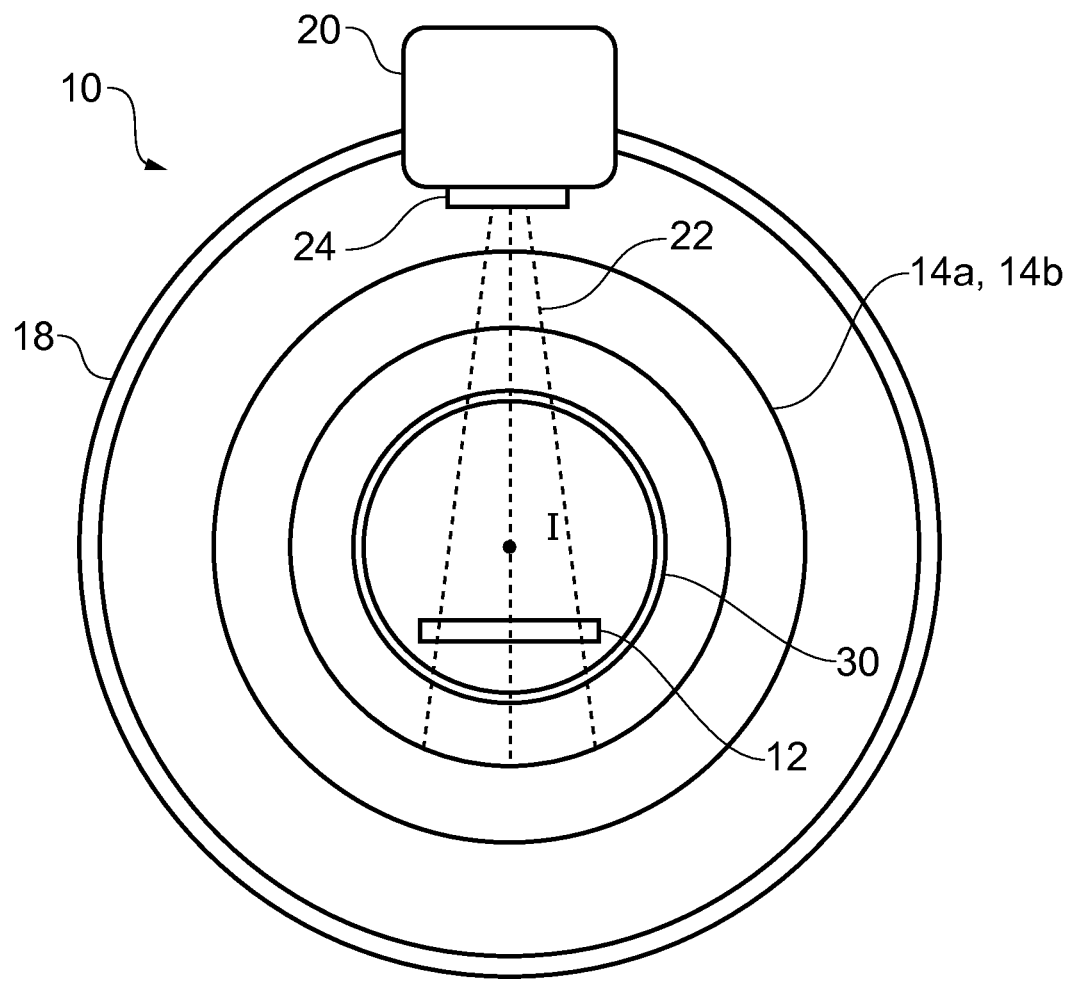
FIG. 1 shows a radiotherapy apparatus according to embodiments of the present invention.

FIG. 1 is a schematic illustration showing the cross-section of a radiotherapy apparatus 10 according to embodiments of the present invention, which combines a radiotherapeutic system with an imaging system.

The apparatus 10 comprises a patient support 12 on which a patient can be supported during treatment. The support 12 is movable in a direction parallel to a horizontal axis (labelled "I", into the page in FIG. 1), such that a patient resting on the support can be moved into and out of the radiotherapy apparatus 10 as required.

The apparatus 10 further comprises an MRI imaging system and this is illustrated schematically in FIG. 1 by magnetic coils 14a, 14b having a central axis coincident with the axis I. As will be understood by those skilled in the art, MRI systems generally comprise a number of magnetic coils for generating primary and gradient magnetic fields. The primary magnetic coil (or coils) generates a strong magnetic field, and the gradient magnetic coil (or coils) fine tunes the magnetic field to take particular magnetic field strength values at different spatial locations. A radio-frequency system generates an RF signal which is used to detect changes of state in hydrogen atoms and thus provide imaging data of the patient. The apparatus 10 may further comprise one or more active shielding coils, which generate a magnetic field outside the coils 14a, 14b of approximately equal magnitude and opposite polarity to the external primary magnetic field. The more sensitive parts of the apparatus 10 can be positioned in this region outside the coils 14a, 14b where the magnetic field is cancelled, at least to a first order. The coils 14a, 14b illustrated in FIG. 1 (and also FIG. 2) are schematic and may be used to generate the primary magnetic field and/or the gradient magnetic field.

Figure 2:
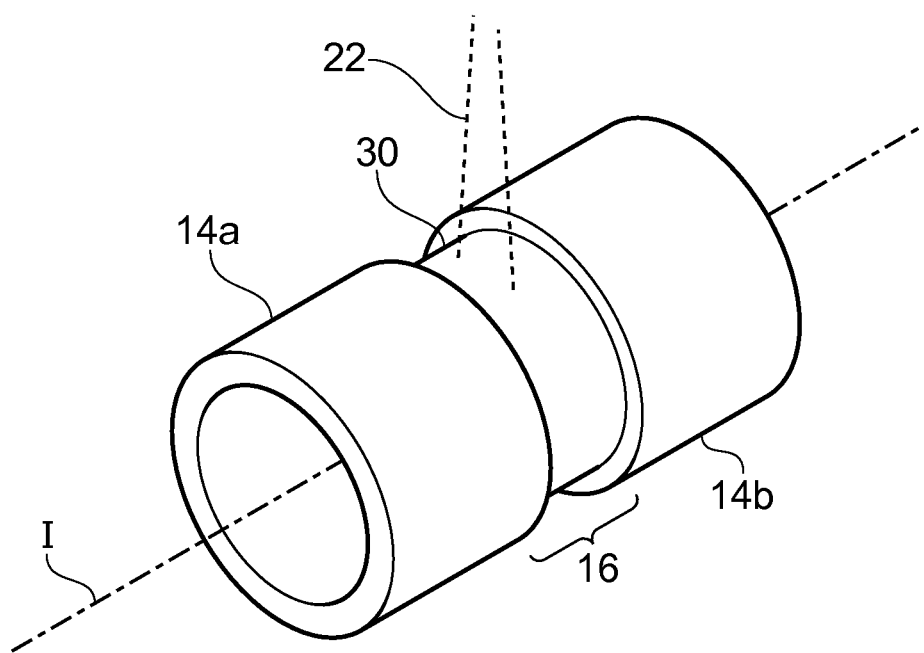
FIG. 2 is a schematic illustration of the arrangement of the radiation detector and the magnetic coils in the radiotherapy apparatus described with respect to FIG. 1.

In one embodiment, as shown most clearly in FIG. 2, the coils 14a, 14b are displaced from each other along the axis I to create a gap 16, or window, between the two coils.

The radiotherapy apparatus 10 further comprises a gantry 18 which supports a radiation head 20. The radiation head comprises a source of radiation (not illustrated) for generating a beam of therapeutic radiation 22. In one embodiment the gantry 18 is rotatable so as to rotate the radiation head around the axis I. The radiation beam is directly generally towards the axis I, and its intersection with that axis is commonly known as the isocentre. The radiation head 20 is arranged so that the radiation beam 22 is directed through the gap 16 between the magnetic coils 14a, 14b. Thus, the radiation head 20 rotates in a plane which lies substantially orthogonal to the axis I and intersects the gap 16. Note that the radiation head 20 and the gantry 18 have been removed from the illustration in FIG. 2 so that the gap 16 between the coils 14a, 14b might be more clearly shown. The radiation beam 22, however, is visible.

The principle of operation is that, by placing the target for treatment on or near the isocentre and rotating the radiation head around the patient, radiation can be directed towards the target from multiple directions. The target is kept within the radiation beam profile throughout the rotation and thus receives a relatively large dose; the surrounding (healthy) tissue falls within the radiation beam profile only at certain angles of rotation and therefore receives a relatively lower dose.

As will be appreciated by those skilled in the art, the source of radiation and the radiation itself can take many forms. For example, a linear accelerator can be used to generate high-energy electron radiation or x-ray radiation (by accelerating the electrons into an x-ray target); in order to have a therapeutic effect, the radiation will typically have an energy of at least 1 MeV. Alternatively, cobalt-60 or other radioactive sources can be used to generate radiation. The present invention is not limited to any particular source of radiation.

The radiation is collimated into a beam shape by primary collimators (not illustrated)—typical shapes include a cone beam or a fan beam—and can then be further collimated by application of one or more secondary collimators 24. In one embodiment the one or more secondary collimators 24 comprise a multi-leaf collimator. These devices comprise one or more banks of thin, laterally-spaced leaves which are individually controllable to move in a longitudinal direction so as to block parts of the radiation beam and so selectively shape the radiation beam. Each leaf can take any one of a range of positions from lying entirely outside the radiation beam at one extreme, to lying entirely across the radiation beam at another extreme. Typically, a multi-leaf collimator will have two banks of such leaves arranged on opposite sides of the radiation beam.

The secondary collimators 24 can be controlled to provide different collimating shapes as the gantry 18 rotates around the patient, so the radiation beam takes an optimal shape at each angle of rotation. For example, the target will not have the same cross section at all angles of rotation so it may be preferable to adapt the shape of the radiation beam as the gantry rotates. This is known as intensity-modulated radiation therapy (IMRT). Real-time imaging data provided by the MRI system may be used to dynamically update the collimation of the radiation beam during treatment in order to track the target more closely.

The positions of the collimating elements and the shape of the radiation beam are thus of crucial importance. A secondary collimator could malfunction or radiation dose may build up unexpectedly during treatment. Such anomalies would have an adverse impact on any patient undergoing therapy, and therefore a device is needed which provides feedback on the radiation beam profile during treatment.

A radiation detector 30 according to embodiments of the present invention is shown in FIGS. 1 and 2—specifically the arrangement of the radiation detector 30 within the radiotherapy apparatus 10.

As can be seen from FIGS. 1 and 2, the radiation detector 30 comprises a hollow tube having a central primary axis which coincides with the axis I. In use, the tube lies within the magnetic coils 14a, 14b, but has a diameter which is sufficient to accommodate the patient support 12 as well as the patient. In other embodiments, however, the tubes may lie outside the magnetic coils 14a, 14b, or even be positioned within them. The tube is positioned such that it extends at least across the gap 16 between the two magnetic coils 14a, 14b and therefore intersects with the radiation beam 22 at all angles of rotation of the gantry 18.

In the illustrated embodiment the hollow tube is cylindrical (that is, it has a circular cross section), but it will be apparent to those skilled in the art from the following description that the tube could take different cross-sectional shapes, such as a square or other regular polygon. A cylindrical tube fits most conveniently within the coils 14a, 14b, however. The tube has at least one open end to allow ingress and egress of a patient (or a part of a patient undergoing therapy). In the illustrated embodiment, both ends of the tube are open.

A plurality of detector elements are arranged over the surface of the tube, and these elements detect the radiation beam 22 as it passes through the walls of the tube. The detector elements may be arranged on the outside surface of the tube, on the inside surface of the tube, or embedded within the walls of the tube or any combination of these possibilities (i.e. some elements on the outside, some embedded and/or some on the inside). As the therapeutic radiation is sufficiently energetic and the walls of the radiation detector are sufficiently radiolucent, the vast majority of the radiation passes through the radiation detector without being sensed. In the arrangement shown in FIGS. 1 and 2, the radiation beam intersects with the walls of the tube, and therefore the radiation is sensed on both sides of the tube. Thus the radiation is sensed both before its interaction with the patient and after its interaction with the patient (where some of the radiation will have been absorbed or scattered by the patient tissue). A comparison between the two sets of data can provide useful clinical feedback on the amount of dose received by the patient.

In one embodiment, the radiation detector 30 can be mounted on the gantry 18 and rotated together with the gantry 18 and the radiation head 20. In this way, the radiation beam 22 will always pass through similar sections on opposite sides of the radiation detector 30, and the detector elements need only be placed in those areas. In other embodiments, it may be easier for the radiation detector 30 not to rotate during therapy, and therefore the detector elements can be arranged over the entire surface of the tube.

The detector elements themselves may comprise any element which is suitable for detecting the radiation beam. For example, the plurality of detector elements may comprise an array of charge-coupled devices (CCDs) arranged over the surface of the tube. Scintillator crystals may be arranged singly or in blocks over the surface of the tube, which scintillate upon interaction with the radiation beam. The scintillated light is generally in the optical range and can therefore be easily detected. Another alternative is to use amorphous silicon detectors: a thin layer of detector material, distributed in pixels over the surface of the tube, and integrated with amplifying circuitry (thin film transistors) to provide a readout.

In one embodiment, the plurality of detector elements comprise optical fibres as shown in FIGS. 3A, 3B, 4A and 4B.

Figure 3A:
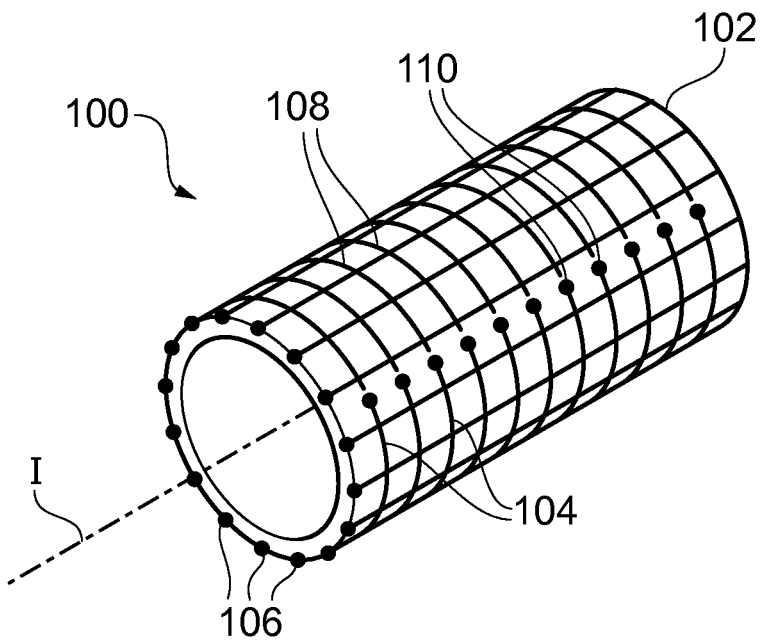
FIGS. 3A and 3B are schematic illustrations of a radiation detector according to embodiments of the present invention.

FIG. 3A shows a radiation detector 100 according to embodiments of the present invention. The radiation detector 100 may be employed within the apparatus 10 as described above with respect to FIGS. 1 and 2. The radiation detector 100 thus comprises a tube 102 and, as described above, this could be cylindrical or take any other shape as appropriate. The tube 102 comprises thin walls, which may be manufactured from plastic or any other suitable material (e.g. polymers such as epoxy).

A plurality of optical fibres are arranged over the surface of the tube 102 in order to detect the radiation passing through the walls of the tube. The fibres may be arranged on the outside of the walls, on the inside of the walls, or embedded within the walls as previously described. A plurality of photodiodes (or other suitable detectors) are coupled to the optical fibres (typically one photodiode for each fibre) to read out the data generated therein.

In one embodiment, each optical fibre comprises a scintillating material which generates photons upon interaction with the radiation beam (typically having a wavelength in the optical range). These photons are then directed optically along the fibre to the photodiode. For example, each fibre may comprise a core of scintillating material surrounded by optical cladding to trap the photons generated therein.

The signal from each fibre corresponds to a line integral of the beam intensity along the path of the fibre over a sampling period. A signal from a single fibre thus provides little definite information on the location of the radiation beam, but rather measures the total radiation deposited in the fibre along its entire length. In order to provide more reliable information, the plurality of optical fibres can be divided into subsets of fibres. Each subset comprises a plurality of fibres running parallel to each other, and the fibres of one subset run at an angle relative to the fibres of the other subset. Signals from multiple fibres can therefore be used to more accurately determine the location of the beam, in that corresponding signals in fibres from different subsets can be used to identify the location of the radiation beam at the intersection of the two fibres.

Figure 3B:
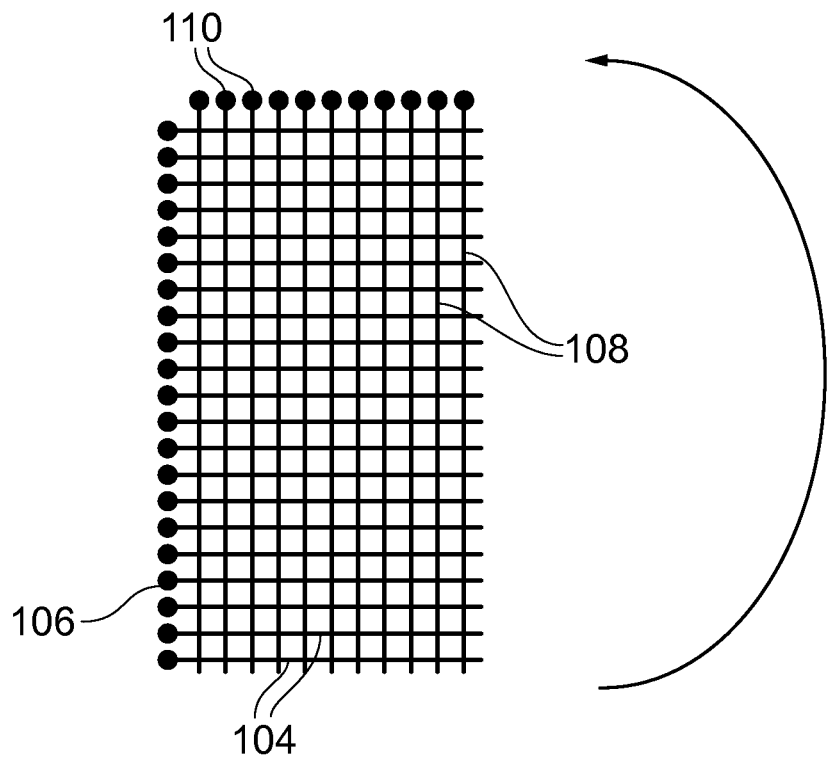

FIG. 3B shows the surface of the detector 100 in FIG. 3A, stretched out in a plan view for clarity. The detector 100 comprises a first subset of optical fibres 104 running substantially parallel to the primary axis I of the tube 102. A corresponding plurality of detectors 106 are coupled to the first subset of fibres 104, and it can be seen from FIG. 3A that, when arranged over the surface of the tube 102, these detectors 106 are arranged around the edge of the tube at one end. A second subset of optical fibres 108 are arranged to run substantially orthogonal to the primary axis I of the tube 102, and a corresponding plurality of detectors 110 are coupled to the second subset of fibres to read out the information collected. It can be seen from FIG. 3A that these detectors 110 run down one side of the tube 102 when arranged over the surface thereof. The grid pattern formed by the first and second subsets of fibres allows a more accurate readout of the location of the radiation beam 22 due to the intersection of the fibres.

Figure 4A:
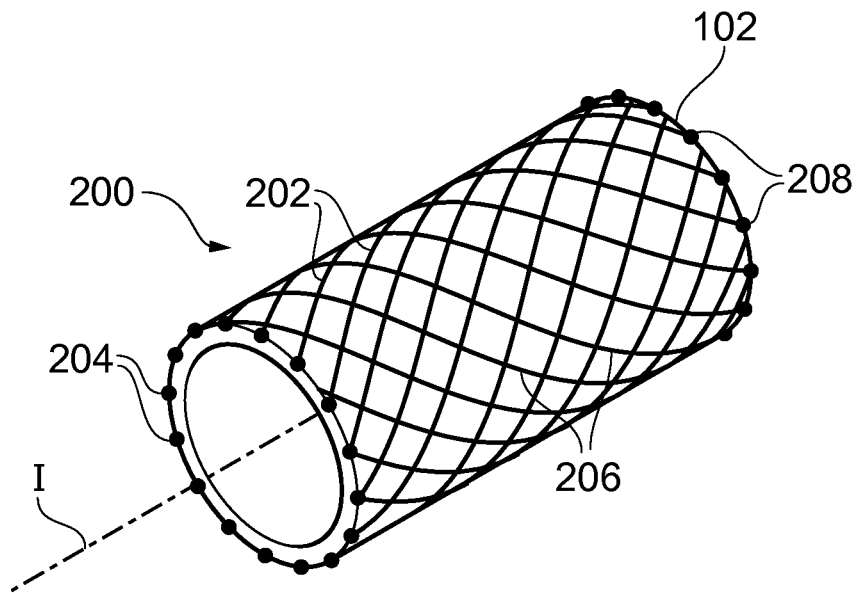
FIGS. 4A and 4B are schematic illustrations of a radiation detector according to further embodiments of the present invention.
Figure 4B:
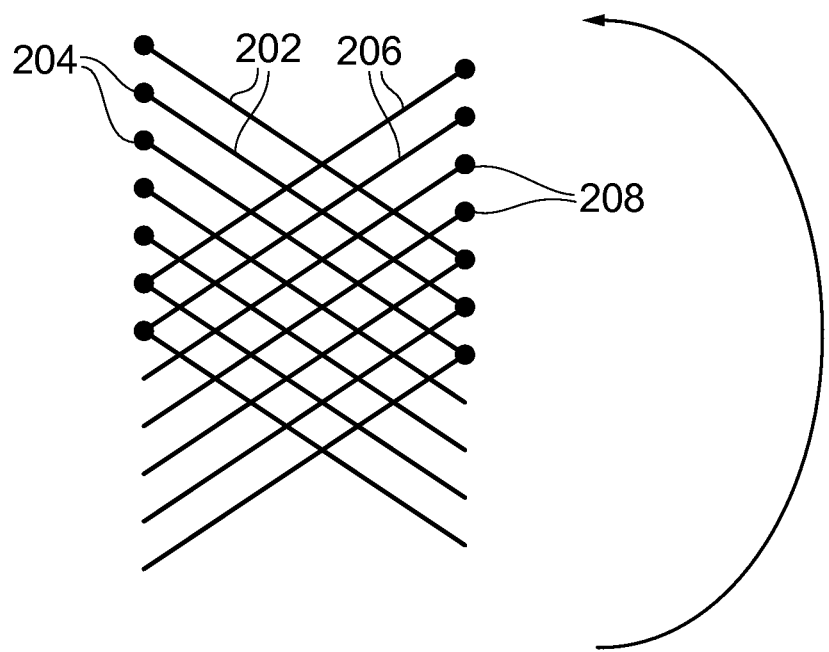

However, the detector 100 described with respect to FIGS. 3A an 3B suffers from the drawback that it is not useable for two angles of rotation, when the radiation beam 22 intersects with the detectors 110. FIGS. 4A and 4B show a radiation detector 200 which does not suffer from this problem. FIG. 4A is a perspective view, while FIG. 4B shows the surface of the detector 200 stretched out in a plan view. Like features are provided with like reference numbers.

The radiation detector 200 again comprises a tube 102 with a primary axis I, and a plurality of optical fibres arranged over the surface of the tube split into two subsets of parallel fibres. Detectors (e.g. photodiodes) are coupled to the fibres to read out the data which is collected.

However, in this embodiment the fibres of at least one of the two subsets are arranged to run at an oblique angle relative to the primary axis I. Where the tube is cylindrical, this means the fibres run along helical paths. In this way, there is no need for the photodiodes to lie across the surface of the tube 102—all photodiodes can be placed at the ends of the tube 102. In the illustrated embodiment, both subsets of fibres are arranged at angles which are oblique to the primary axis I. This means that the two subsets of fibres can run orthogonal to each other, which reduces the complexity of data processing.

Thus, the detector 200 comprises a first subset of optical fibres 202 which run at an oblique angle relative to the primary axis I. Where the tube 102 is cylindrical, as illustrated, this results in each fibre of the first subset 202 taking a right-handed helical path. A corresponding plurality of detectors (e.g. photodiodes) 204 are coupled to the ends of the fibres and arranged around a first end of the tube 102. The detector 200 also comprises a second subset of optical fibres 206 which also run at an oblique angle relative to the primary axis I, and at an angle relative to the fibres of the first subset 202. Where the tube 102 is cylindrical, as illustrated, this results in each fibre of the second subset 206 taking a left-handed helical path. A corresponding plurality of detectors (e.g. photodiodes) 208 are coupled to the ends of the fibres and arranged around a second end of the tube 102.

The radiation detector 200 has no photodiodes which lie within the surface of the tube 102, and can therefore be used at all angles of rotation.

The angle of the fibres (or the pitch of the helix for embodiments utilizing a cylindrical tube) is sufficient that the radiation beam which intersects the radiation detector 200 does not intersect the same fibre more than once.

In one embodiment the fibres are spaced approximately 5 mm apart in order to get an adequate resolution. In a tube which is 600 mm in diameter, and with two subsets of fibres, this leads to a total number of approximately 750 fibres.

Figure 5:
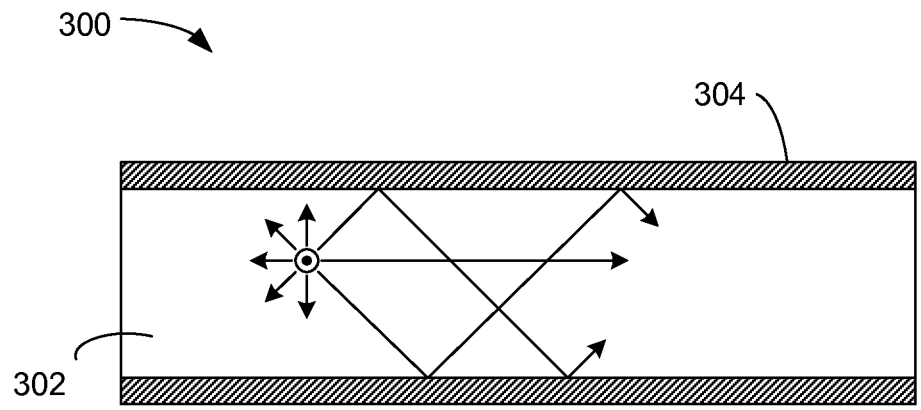
FIG. 5 shows an optical fibre according to embodiments of the present invention.

FIG. 5 shows a cross-section through an optical fibre 300 according to embodiments of the present invention, which may be used in conjunction with any of the radiation detectors described above.

The fibre 300 comprises an inner core of scintillating material 302 which is surrounded by optical cladding 304 (such as glass). A photon from the radiation beam 22 passes through the scintillating material and a burst of optical radiation is produced as a result, travelling in all directions. A portion of the optical photons are trapped in the fibre through total internal reflection in the optical cladding 304, and these travel down the fibre 300 where they can be collected by detectors as described above.

Figure 6:
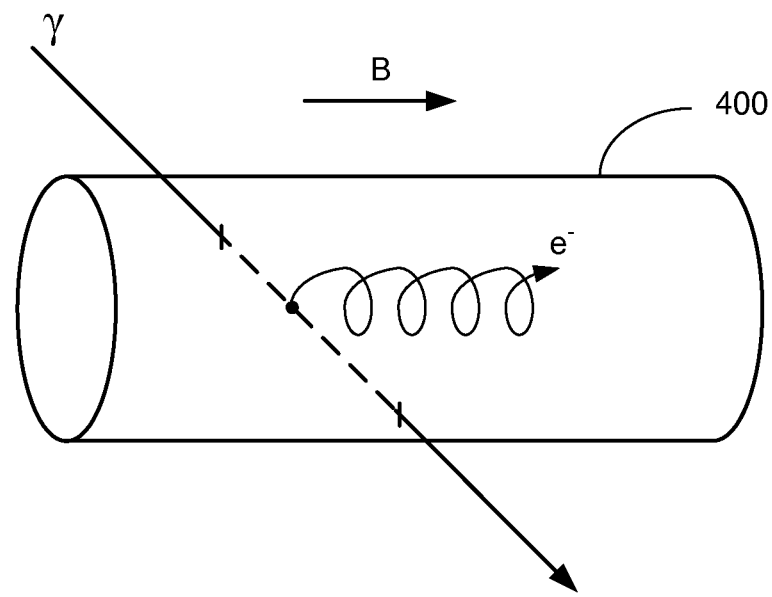
FIG. 6 shows an optical fibre according to further embodiments of the present invention.

Another detection mechanism is illustrated in FIG. 6, which shows another optical fibre 400 according to embodiments of the present invention. The optical fibre 400 need not comprise scintillating material.

An energetic photon from the radiation beam intersects the optical fibre 400 (at right angles in this example), and generates a secondary electron through interaction with the material in or nearby the fibre 400. In therapeutic applications, the radiation beam may have a nominal energy of approximately 6 MV, with a peak of photon flux at approximately 1.2 MeV photons. The secondary electrons produced by interaction with such a photon will have energies in a range up to 1.2 MeV. At these energies, where the secondary electrons move faster than the speed of light in the local medium, the electrons produce radiation according to the Cherenkov effect. That is, for the example of a pure glass optical fibre, electrons that have an energy in excess of 0.2 MeV (at which point they travel faster than light in glass) will emit Cherenkov radiation. Such radiation can be trapped in the optical fibre through total internal reflection, and then detected by the detectors as described above.

The amount of Cherenkov radiation that is emitted by a single electron is related to the amount of time that electron travels in the optical fibre (i.e. in the glass). In order to improve the efficiency of detection via the Cherenkov radiation, the optical fibre 400 and the radiation detector itself may be adapted to increase the amount of time secondary electrons spend in the fibre, i.e. to increase the path length of the electron in the fibre 400. For example, when the fibre is positioned in a magnetic field (such as in the apparatus described in FIGS. 1 and 2), the secondary electrons accelerate in a direction which is orthogonal to the magnetic field lines. That is, the electrons move in a helical path along the direction of the magnetic field (assuming they have some component of velocity in a direction parallel to the magnetic field), making orbits of radius equal to the Larmor radius.

For a 1 MeV secondary electron (i.e. approximately the most one would expect from a 6 MV photon beam) in a 1.5 T magnetic field, the Larmor radius is equal to 2.2 mm. Thus, by making the radius of the optical fibre 400 thicker than would ordinarily be the case (i.e. to a radius which is of a similar order of magnitude to the Larmor radius or greater), the path length of the secondary electrons within the optical fibre can be extended. For example, the radius of the optical fibre may be within a range from 1 mm to 3 mm.

Further, it will be apparent that the secondary electrons move in a direction which is parallel to the magnetic field (albeit that they process helically in that direction). Thus, by ensuring that the optical fibres run in a direction which is parallel to the magnetic field lines (or by preferably running the optical fibres in a direction which is near parallel to the magnetic field lines), the electrons can be kept within the optical fibre for an increased period of time, and a greater portion of the Cherenkov radiation which is emitted will be captured within the fibre 400. For example, when placed in an MRI system as shown in FIGS. 1 and 2, the subset of fibres 104 shown in FIGS. 3A and 3B are parallel to the magnetic field and therefore capture this radiation most efficiently. The fibres 202, 206 of the detector shown in FIGS. 4A and 4B are less efficient at capturing the Cherenkov radiation, but are still reasonably close to running parallel to the magnetic field (for example in comparison to the fibres 108).

The optical fibre 400 can thus capture Cherenkov radiation efficiently when oriented parallel to a local magnetic field, and does not require a scintillating material in order to operate. However, it will be apparent to those skilled in the art that the optical fibre 400 may nonetheless comprise scintillating material, and the orientation of the fibre parallel to the magnetic field serves to increase the interactions of secondary electrons with the scintillating material, increasing the likelihood that a particular photon will be detected.

Although described above with respect to a combined radiotherapy—MRI apparatus, it will be apparent to those skilled in the art that the radiation detectors described herein can be used to detect radiation from any radiotherapy or radiography (i.e. imaging) system. While the radiation detectors are particularly compact and therefore suited to use in the narrow dimensions of MRI magnetic coils, they can be employed in any apparatus which generates a beam of radiation for therapeutic or imaging purposes.

The present invention provides a radiation detector which comprises a tube and detector elements distributed over the tube. Such an arrangement can be used to provide information on a radiation beam prior to interaction with a patient and after interaction with the patient. The detector is particularly compact and therefore suited to use with apparatus where space is restricted. By a particular arrangement of detectors and optical fibres, the detector can provide data at all angles of rotation.

Those skilled in the art will appreciate that various amendments and alterations can be made to the embodiments described above without departing from the scope of the invention as defined in the claims appended hereto.

The invention claimed is:

1. A radiation detector for use in a system having a source of radiation, the source of radiation generating a beam of radiation along a beam axis for intersecting with a patient or part of a patient, the radiation detector comprising:
   a hollow tube in which the patient or the part of the patient can be positioned, the hollow tube having a primary axis which, in use, lies transverse to the beam axis; and
   a plurality of optical fibres distributed over the surface of the hollow tube for detecting the radiation beam.

2. The radiation detector according to claim 1, wherein the plurality of optical fibres are distributed over the surface of the hollow tube for detecting the radiation beam prior to its impact with the patient, and for detecting the radiation beam after its impact with the patient.

3. The radiation detector according to claim 2, wherein the plurality of optical fibres are distributed over the surface of the hollow tube at least in a first area, for detecting the radiation beam prior to its impact with the patient, and a second area diametrically opposite the first area, for detecting the radiation beam after its impact with the patient.

4. The radiation detector according to claim 3, wherein the plurality of optical fibres are distributed over substantially the entire surface of the hollow tube.

5. The radiation detector according to claim 1, wherein the plurality of optical fibres comprises a first subset of optical fibres running substantially parallel to each other, and a second subset of optical fibres running substantially parallel to each other and transverse to the first subset of optical fibres.

6. The radiation detector according to claim 5, wherein at least one of the first and second subsets of optical fibres runs at an angle which is oblique to the primary axis of the tube.

7. The radiation detector according to claim 5, wherein the first subset of optical fibres runs substantially orthogonal to the second subset of optical fibres.

8. The radiation detector according to claim 5, wherein at least one of the first and second subsets of optical fibres runs substantially parallel to the primary axis of the hollow tube.

9. The radiation detector according to claim 1, wherein the plurality of optical fibres scintillate upon interaction with the radiation beam.

10. The radiation detector according to claim 1, further comprising a plurality of read-out devices coupled to the plurality of optical fibres.

11. The radiation detector according to claim 10, wherein the plurality of read-out devices comprises a first subset of read-out devices arranged towards a first end of the hollow tube, and a second subset of read-out devices arranged towards a second end of the hollow tube.

12. The radiation detector according to claim 1, wherein the plurality of optical fibres are embedded within a wall of the hollow tube.

13. The radiation detector according to claim 1, wherein the hollow tube is manufactured from a substantially radiolucent material.

14. The radiation detector according to claim 1, wherein the tube is cylindrical.

15. An apparatus, comprising:
   a source of radiation, for generated a radiation beam along a beam axis;
   a patient support, for supporting a patient; and
   a radiation detector comprising:
      a hollow tube in which the patient support can be arranged, the hollow cylinder having a primary axis which, in use, lies transverse to the beam axis; and
      a plurality of optic fibers distributed over the surface of the hollow tube for detecting the radiation beam.

* * * * *